US00PP28174P2

(12) United States Plant Patent
Pan

(10) Patent No.: US PP28,174 P2
(45) Date of Patent: Jul. 11, 2017

(54) ***LANTANA* PLANT NAMED 'LANZ0007'**

(50) Latin Name: ***Lantana camara* L.**
Varietal Denomination: LANZ0007

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 76 days.

(21) Appl. No.: 14/545,541

(22) Filed: May 19, 2015

(30) Foreign Application Priority Data

Jun. 18, 2014 (QZ) ..... PBR 2014/1617

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Anne Grunberg
(74) *Attorney, Agent, or Firm* — Dale Skalla

(57) ABSTRACT

A new *Lantana* plant named 'LANZ0007' particularly distinguished large sized golden yellow to orange flowers with an orange throat, dark green foliage, dense mounding habit, early flowering, excellent floriferousness, and good heat tolerance compared with control.

1 Drawing Sheet

Latin name of the genus and species of the plant claimed: *Lantana camara* L.

Varietal denomination: 'LANZ0007'.

BACKGROUND OF THE NEW PLANT

The present invention comprises a new *Lantana*, botanically known as *Lantana camara* L., and hereinafter referred to by the variety name 'LANZ0007'.

'LANZ0007' is a product of a planned breeding program. The new cultivar 'LANZ0007' has large golden yellow to orange flowers with an orange throat, early flowering and excellent floriferousness, dark green foliage, dense mounding habit, and good heat tolerance.

'LANZ0007' originates from the self-pollination of a plant designated as 'LCE665-1' made in July 2009 in a greenhouse in Gilroy, Calif., USA. The parent 'LCE665-1' has yellow flower color, a bushy plant habit, and displays taller growth than 'LANZ0007'.

The resulting seed was sown in June 2010 in a greenhouse in Gilroy, Calif. and 'LANZ0007' was selected as one flowering plant within the progeny of the stated cross in November 2010.

The first act of asexual reproduction of 'LAN0007' was accomplished when vegetative tip cuttings were propagated from the initial selection in December 2010 in a greenhouse in Gilroy, Calif.

BRIEF SUMMARY OF INVENTION

Horticultural examination of plants grown from cuttings of the plant initiated in the spring of 2011 in Gilroy, Calif., and continuing thereafter, has demonstrated that the combination of characteristics as herein disclosed for 'LANZ0007' are firmly fixed and are retained through successive generations of asexual reproduction.

'LANZ0007' has not been observed under all possible environmental conditions. The phenotype may vary significantly with variations in environment such as temperature, light intensity, and day length.

A Plant Breeder's Right for this cultivar was applied with the European Union Office (CPVO) on Jun. 18, 2014; No. 2014/1617.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0007' with colors being as true as possible with an illustration of this type.

Figure 1:
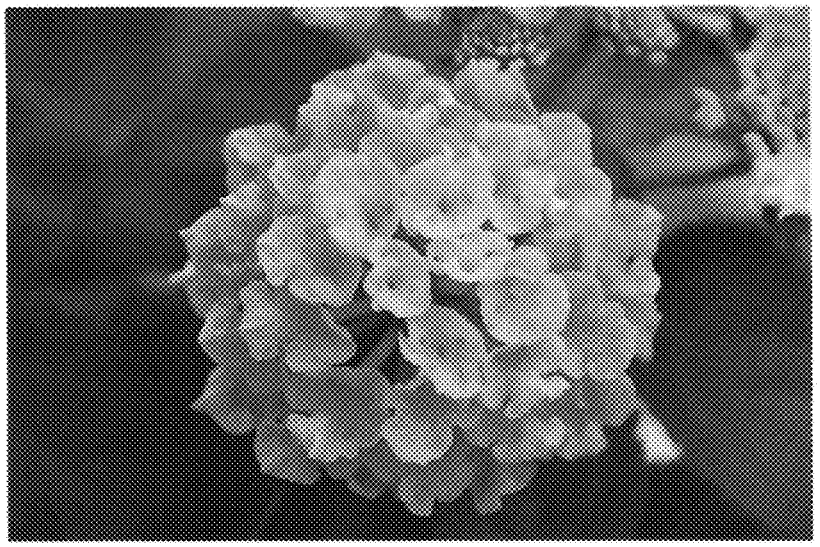
Figure 2:
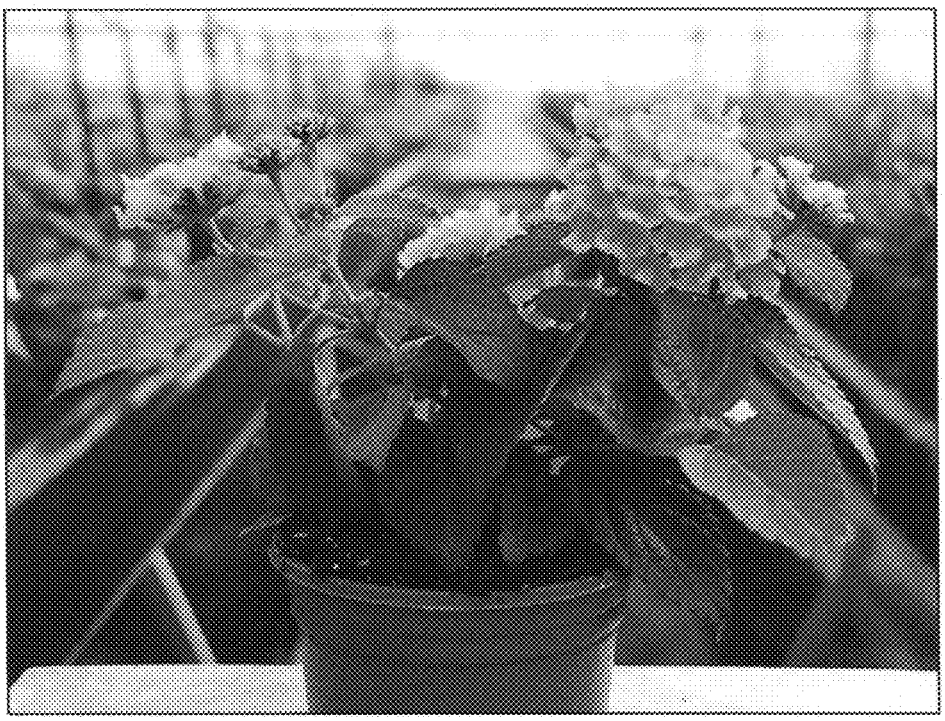

The photographic drawings show in FIG. 1 a close view of an inflorescence and in FIG. 2 a young flowering plant.

DETAILED BOTANICAL DESCRIPTION

The plant descriptions and measurements were taken in Gilroy, Calif. in November 2014. The plants were approximately 6 months old and were growing in 1 gallon pots in a greenhouse.

The aforementioned photographs FIGS. 1 and 2 were taken in mid-April in Andijk, Netherlands. The plant is about 12 weeks old.

Color references are made to The Royal Horticultural Society Colour Chart (R.H.S.) 2001.

TABLE 1

DIFFERENCES BETWEEN THE NEW VARIETY 'LANZ0007' AND TWO MOST SIMILAR VARIETIES

| | 'LANZ0007' | 'BALUCGOLD', U.S. Plant Pat. No. 14,634, also known as 'Lucky Gold' |
|---|---|---|
| Leaf length: | 7.5-7.8 cm | 6 cm |
| Inflorescence, diameter: | 5 cm | 4 cm |
| Main color: | Orange with golden and yellow hues | Gold |
| Plant habit: | More compact and more branches | More open habit with fewer and longer branches |
| | 'LANZ0007' | 'LANZ0002', U.S. Plant Pat. No. 23,317, Commercially known as 'Bandana Peach' |
| Flower, overall color | Orange with golden and yellow hues: RHS 25A, 23A and 15A | Light orange with pink hues: RHS 7A overlain with tones of N25A to N25C, and 51A to 51C near margins |

Plant:

*Form, growth and habit*.—Semi-woody, grown as an annual or perennial; compact and dense mounding habit; well branched.

*Plant height*.—28-30.0 cm.

*Plant height* (*inflorescence included*).—29-32.0 cm.

*Plant width*.—36-42.0 cm.

Foliage:

*Type*.—Opposite.

*Immature leaf, color upper surface*.—Closest to RHS 139A.

*Immature leaf, color lower surface*.—Closest to RHS 137A.

*Mature leaf, color upper surface*.—Closest to RHS 147A.

*Mature leaf, color lower surface*.—Closest to RHS 147B.

*Length*.—7.5-7.8 cm.

*Width*.—4.4-4.7 cm.

*Shape*.—Elliptic.

*Base shape*.—Rounded.

*Apex shape*.—Mucronate.

*Margin*.—Dentate.

*Texture, upper*.—Hirsute.

*Lower surface*.—Hirsute.

*Lower surface*.—RHS 147B.

*Pattern of veining*.—Pinnate.

*Petioles color*.—RHS 147B.

*Petioles length*.—0.9-1.4 cm.

*Diameter of petiole*.—0.2 cm.

*Texture* (*upper and lower surface*).—Hirsute with some very short glandular hairs.

Stem:

*Color of stem*.—RHS 147B.

*Length of stem*.—22-25.0 cm.

*Diameter*.—0.45 cm.

*Length of internodes*.—1.6-2.3 cm.

*Texture*.—Pilose, hirsute.

Inflorescence:

*Type*.—Umbel like, flattened semi-sphere the florets are sessile on an ovate receptacle.

*Blooming habit*.—Flowers continuously from spring through fall.

*Number of open flowers per inflorescence*.—28-32.

*Quantity of inflorescences per plant*.—About 10 (with open florets).

*Lastingness of individual blooms on the plant*.—About 4 weeks (depending on temperatures).

*Fragrance*.—Slightly spicy.

*Umbel horizontal diameter*.—About 5 cm.

*Umbel vertical height*.—2.5-2.8 cm.

*Peduncle color*.—RHS 147B.

*Length of peduncle*.—5.3-6.4 cm.

*Peduncle diameter*.—0.2 cm.

*Texture*.—Hirsute, glandular hairs.

Flower:

*Floret form*.—Corolla salver-shaped to shallow cup-shaped, with a relatively long tube at the base; each flower subtended by a single bract.

*Length of floret*.—1.8-2.2 cm.

*Width of floret*.—1.0-1.1 cm.

*Depth of floret*.—0.7-1.1 cm.

*Young floret, color upper surface*.—RHS 15A and RHS 15B.

*Young floret, color lower surface*.—RHS 15D.

*Mature florets, color upper surface*.—RHS 23A outer petal and RHS 25A near throat.

*Mature floret, color lower surface*.—RHS 23D overlain with RHS 168C.

*Apex shape*.—Rounded and slightly crenate.

*Degree of lobation*.—Moderate.

*Margin*.—Crenate.

*Base*.—Fused.

*Texture, upper surface*.—Papillose.

*Lower surface*.—Papillose.

*Tube, color outer surface*.—Closest to RHS 172C.

*Tube, color inner surface*.—Closest to RHS 162A.

*Tube, length*.—1.3 cm.

*Tube, diameter* (*at opening*).—0.2 cm.

*Tube, texture outer surface*.—Pubescent.

*Inner surface*.—Hirsute.

Bud (just before opening):

*Color*.—Starting at RHS 16A and maturing to 25C.

*Length*.—0.9-1.5 cm.

*Width*.—0.4-0.6 cm at the apex.

*Shape*.—Tubular with a flared apex.

Bract:

*Color*.—Closest to RHS 146A.

*Length*.—0.8-1.0 cm.

*Diameter*.—0.15-0.2 cm.

*Texture, upper surface*.—Hirsute.

*Lower surface*.—Hirsute.

Calyx:

*Number of sepals*.—5, fused sepals forming a short tube around the base of the floret.

*Color of sepals*.—RHS 146D.

*Length of sepals*.—0.3 cm.

*Width of sepals*.—0.2 cm.

*Apex shape*.—Acuminate.

*Apex margins*.—Entire.

*Texture, outer surface*.—Pubescent.

*Inner surface*.—Glabrous.

Reproductive organs:

*Gynoecium*.—Pistil quantity: One. Length: 0.5 cm. Style color: RHS 145D. Style length: 0.3 cm. Stigma color: RHS 145A. Ovary color: RHS 146B. Ovary length: 0.1 cm. Ovary diameter: 0.1 cm.

*Androecium*.—Stamen quantity: 4. Color of filaments: RHS 162C. Length filaments: 0.15-0.2 cm. Anther color: RHS 163A. Length of anthers: 0.1 cm. Color of pollen: RHS 10B. Pollen amount: Normal.

*Fertility/seed set*.—Has not been determined to date.

*Disease/pest resistance*.—Has not been determined to date.

What is claimed is:

1. A new and distinct variety of *Lantana* plant named 'LANZ0007' substantially as illustrated and described herein.

* * * * *